United States Patent
Thacker et al.

(10) Patent No.: US 7,363,079 B1
(45) Date of Patent: Apr. 22, 2008

(54) POWER QUALIFIER FOR ELECTRICAL STIMULATION CONFIGURATIONS

(75) Inventors: James R Thacker, Eureka, MO (US); Kerry Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 553 days.

(21) Appl. No.: 10/672,660

(22) Filed: Sep. 25, 2003

Related U.S. Application Data

(60) Provisional application No. 60/413,829, filed on Sep. 26, 2002.

(51) Int. Cl.
*A61N 1/36* (2006.01)
(52) U.S. Cl. ........................................ 607/27
(58) Field of Classification Search ............... None
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 3,822,708 A | 7/1974 | Zilber | |
| 4,735,204 A | 4/1988 | Sussman et al. | |
| 5,350,412 A | 9/1994 | Hoegnelid et al. | |
| 5,735,887 A | 4/1998 | Barreras, Sr. et al. | |
| 5,782,880 A | 7/1998 | Lahtinen et al. | |
| 5,785,660 A * | 7/1998 | van Lake et al. | 600/523 |
| 5,895,416 A | 4/1999 | Barreras, Sr. et al. | |
| 6,393,325 B1 | 5/2002 | Mann et al. | |
| 6,738,668 B1 * | 5/2004 | Mouchawar et al. | 607/28 |
| 6,934,583 B2 * | 8/2005 | Weinberg et al. | 607/9 |
| 2002/0138124 A1 | 9/2002 | Heifer et al. | |
| 2003/0093134 A1 * | 5/2003 | Bradley | 607/72 |

FOREIGN PATENT DOCUMENTS

WO    WO-02/096512 A1    12/2002

* cited by examiner

*Primary Examiner*—Carl Layno
*Assistant Examiner*—Jon-Eric Morales
(74) *Attorney, Agent, or Firm*—Vista IP Law Group LLP

(57) ABSTRACT

At least one system and at least one method permit a clinician to view or hear power consumption data during a Spinal Cord Stimulation (SCS) system fitting procedure. For example, a clinician's programming computer includes a display of power consumption for each effective stimulation configuration under evaluation during fitting. A clinician performing the fitting procedure uses a programming computer to select various stimulation configurations. The power consumption of the SCS configuration(s) presently and/or previously exercised is displayed for the clinician. By comparing the power consumption for each configuration, the clinician may select a configuration consuming less power while providing effective therapy. Suggestions for low power configurations may be provided by the programming computer.

31 Claims, 7 Drawing Sheets

POWER QUALIFIER FOR ELECTRICAL STIMULATION CONFIGURATIONS

The present application claims the benefit of U.S. Provisional Patent Application Ser. No. 60/413,829, filed Sep. 26, 2002, which application is incorporated herein by reference in its entirety.

FIELD OF THE INVENTION

The present invention relates to the selection of stimulation parameter sets for electrical stimulation systems, and more particularly to systems and methods for communicating the power consumption levels of various Spinal Cord Stimulation (SCS) system configurations evaluated during an SCS system fitting procedure.

BACKGROUND OF THE INVENTION

Spinal cord stimulation is a well accepted clinical method for reducing pain in certain populations of patients. A Spinal Cord Stimulation (SCS) system typically includes an Implantable Pulse Generator (IPG), electrodes, at least one electrode lead, and, optionally, at least one electrode lead extension. The electrodes, which reside on a distal end of the electrode lead, are typically implanted along the dura of the spinal cord, and the IPG generates electrical pulses that are delivered through the electrodes to the nerve fibers within the spinal column. Individual electrode contacts (the "electrodes") are arranged in a desired pattern and spacing in order to create an electrode array. Individual wires within one or more electrode leads connect with each electrode in the array. The electrode lead(s) exit the spinal column and generally attach to one or more electrode lead extensions. The electrode lead extensions, in turn, are typically tunneled around the torso of the patient to a subcutaneous pocket where the IPG is implanted. Alternatively, the electrode lead may directly connect with the IPG.

SCS and other stimulation systems are known in the art. For example, an implantable electronic stimulator is disclosed in U.S. Pat. No. 3,646,940, issued Mar. 7, 1972, entitled "Implantable Electronic Stimulator Electrode and Method," teaches timed sequenced electrical pulses to a plurality of electrodes. Another example, U.S. Pat. No. 3,724,467, issued Apr. 3, 1973, entitled "Electrode Implant for the Neuro-Stimulation of the Spinal Cord," teaches an electrode implant for neuro-stimulation of the spinal cord. A relatively thin and flexible strip of biocompatible material is provided as a carrier on which a plurality of electrodes reside. The electrodes are connected by a conductor, e.g., a lead body, to an RF receiver, which is also implanted and is controlled by an external controller.

In U.S. Pat. No. 3,822,708, issued Sep. 9, 1974, entitled "Electrical Spinal Cord Stimulating Device and Method for Management of Pain," teaches an SCS device with five aligned electrodes which are positioned longitudinally along the spinal cord. Current pulses applied to the electrodes block sensed intractable pain, while allowing passage of other sensations. The stimulation pulses applied to the electrodes have a repetition rate of 5 to 200 pulses per second. A patient-operated switch allows the patient to change the electrodes that are activated (i.e., which electrodes receive the stimulation pulses from the IPG) in order to stimulate a specific area of the spinal cord, as required, to better block the pain.

An SCS system treats chronic pain by providing electrical stimulation pulses through the electrodes of an electrode array to the nerve fibers of the spinal cord. The electrode array is situated within the epidural space of the spinal cord. A clinician defines the characteristics of the stimulation pulses by adjusting various stimulation parameters, thereby changing the location and manner of stimulation to the tissue of the spinal cord. A clinician may determine an effective stimulation parameter configuration based on the feedback of the patient to various stimulation configurations. This process of adjusting stimulation parameters to determine the most effective configuration of a parameter set is known as an SCS system fitting procedure.

Two of the most important issues encountered during an SCS system fitting procedure are comfort and power consumption. Comfort is essential to a patient, for this is the purpose of the SCS system implantation: to relief pain. During the fitting session, multiple stimulation parameter configurations may be identified which demonstrate similar comfort levels, or paresthesia benefits, for the patient. However, each of these configurations of similar comfort likely consumer power at very different rates.

Selecting a configuration with minimal power consumption is essential to prolonging the effective life of a battery-powered IPG in an SCS system. If a configuration depletes the battery power of the IPG too quickly, the IPG will require more frequent and longer battery recharging sessions. The more frequent and longer the battery recharging sessions, the sooner the patient will be required to endure another intrusive operation to remove the IPG and replace it with a new IPG.

As mentioned earlier, configurations that seem to provide equal paresthesia to a patient may consume power at very different rates. Yet, for each of these given parameter configurations, there is no immediate information given to the clinician regarding the power consumption for each configuration. Thus, it is difficult for the clinician to compare the power consumption efficacy of one parameter configuration to another. There is also no method for using the power consumption measurements of configurations that have been evaluated to guide the clinician to a lower power consumption configuration with equal paresthesia benefits.

What is needed is an indication of the power consumption for each stimulation parameter configuration being evaluated, and a method for using the power consumption information to help locate a low power consumption configuration.

SUMMARY OF THE INVENTION

The present invention addresses the above and other needs by providing at least one system for displaying power consumption data, e.g., through a clinician's computer or fitting station, and at least one method for finding an effective configuration with low power consumption. When a Spinal Cord Stimulation (SCS) system is implanted in a patient, a fitting procedure is performed to determine an effective SCS configuration for the patient. The clinician performing the fitting procedure uses a programming computer to adjust various stimulation parameters and select various stimulation configurations of parameter sets. The power consumption of each configuration presently and/or previously exercised is displayed for the clinician. The clinician may either choose a configuration already exercised based on the display, or use the information on the display to guide the selection of subsequent test configurations. Suggestions may also be generated by the computer to guide the clinician to low power consumption configurations.

In accordance with one aspect of the present invention, the clinician is provided a measure of power consumption to facilitate comparison of various SCS configurations. Power consumption is an important parameter for comparison because the effective life of the implant is directly related to its level of power consumption, and different stimulation configurations consume power at different rates. High levels of power consumption may result in early battery or implant replacement or, in the case of rechargeable systems, more frequent or longer recharging sessions and eventual battery or implant replacement. Replacing the battery or implant forces the patient to endure another intrusive, expensive, and uncomfortable operation. Advantageously, a power consumption display for the clinician allows the clinician to maintain appropriate paresthesia for the patient while selecting a low power consumption configuration, thereby maximizing the effective life span of the implant and minimizing the risk that a patient will be required to endure another operation.

In accordance with another aspect of the present invention, a means of communication, such as a navigation display, provides power consumption data to a clinician. The navigation display is used as a means for displaying different stimulation configurations. Displaying the power consumption on the navigation screen provides a natural environment for the clinician to view the overall performance of the stimulation configurations being evaluated and reduces the time and effort required to identify low power consumption configurations.

In accordance with another aspect of the present invention, the system may communicate power consumption data using audio or visual signals through speakers or on a display, such as the navigation display. The power consumption data may be communicated using iso-power contour lines, intensity, color, text, numerical measures, pitch, sound frequency, volume, or other indications capable of communicating relative levels of power consumptions for a variety of SCS system configurations. Thus, the clinician is provided simple audio or visual feedback regarding which configurations provide both effective stimulation and low power consumption.

In accordance with another aspect of the present invention, power consumption is co-optimized, or compared, with other stimulation parameters. Often during a patient fitting, more than one configuration is found that provides effective stimulation. The clinician marks these configurations on the navigation display, or other means, and can return to each of these configurations in order to evaluate their power consumption efficacy in light of other parameters. Any stimulation parameter, including measurements of therapeutic efficacy of stimulation, i.e., provided by the Visual Analog Scale (VAS) for pain and/or binary comparisons made by the patient, can be co-optimized with the power consumption to yield the best trade-off stimulation configuration. Communicating all the relevant parameters with power consumption on the navigation display, or compatible communication means, allows the clinician to easily perform the co-optimization.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figures 1, 2:
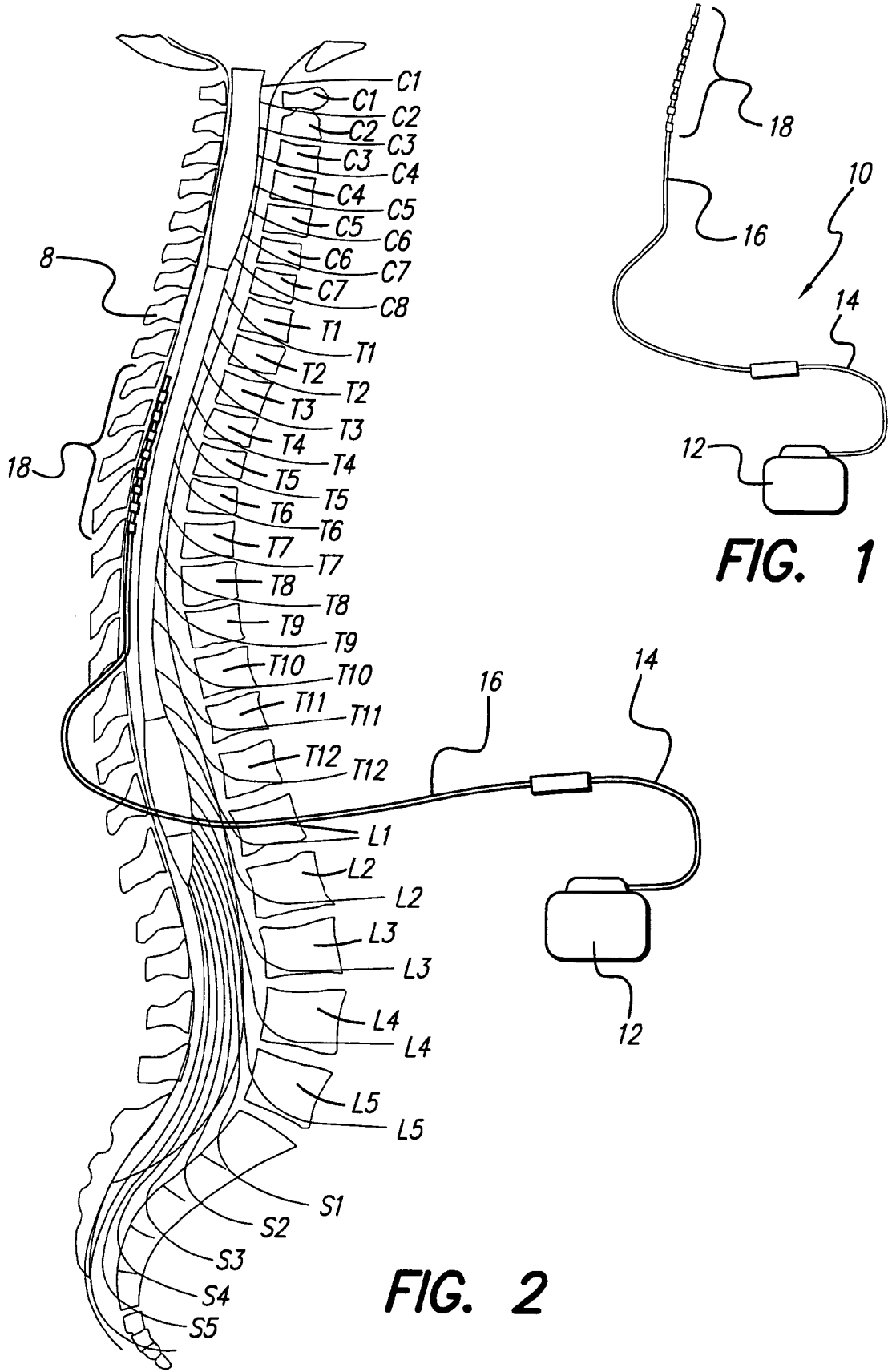
FIG. 1 depicts a typical Spinal Cord Stimulation (SCS) system including an Implantable Pulse Generator (IPG) and an electrode array.
FIG. 2 depicts the SCS system of FIG. 1 implanted in a spinal column.

The power qualifier of the present invention provides an improved display and cues for a clinician who is fitting a Spinal Cord Stimulation (SCS) system to a patient. Such display and cues may be used during the fitting of an SCS system 10 as shown in FIG. 1. The SCS system 10 typically comprises an Implantable Pulse Generator (IPG), or stimulator, 12; optionally, at least one lead extension 14; and at least one lead 16 that includes at least one electrode array 18. The IPG 12 generates stimulation current or voltage for the implanted electrodes that make up the electrode array 18. A proximal end of the lead extension 14 is removably connected to the IPG 12. A distal end of the lead extension 14 is removably connected to a proximal end of the lead 16. And, the electrode array 18 resides on a distal end of the lead 16. The in-series combination of the lead extension 14 to the lead 16, carries the stimulation current from the IPG 12 to the electrode array 18.

FIG. 2 shows the SCS system 10, described in FIG. 1 above, implanted in a spinal column 8. The electrode array 18 is implanted within the epidural space of the spinal column next to nerves that are the target of stimulation. Due to the lack of space near the location where the lead 16 exits the spinal column 8, i.e, the lead exit point, the IPG 12 is generally implanted in the abdomen or above the buttocks.

The lead extension 14 is long enough to permit the IPG 12 to be implanted in a suitable location distanced from the lead exit point.

While the implantable system depicted in FIGS. 1 and 2 comprises a separate lead extension 14 electrically connecting the lead 16 to the IPG 12, the present invention also applies to stimulation systems with at least one electrode lead connected directly to a pulse generator. Other embodiments of the present invention apply to stimulation systems with one or more optional lead extensions and one or more leads each having one or more electrode arrays of at least one electrode per array.

Figure 3A:
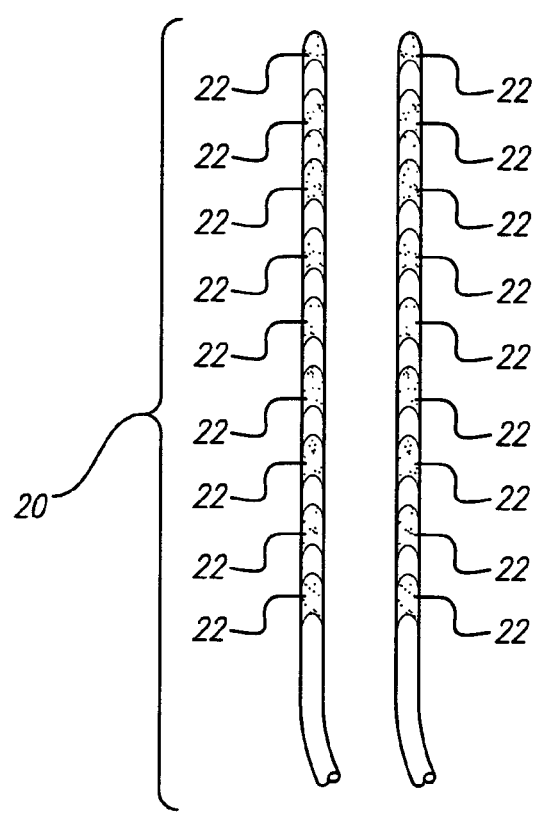
FIG. 3A shows a pair of in-line electrode arrays used to provide two dimensional stimulation.
Figure 3B:
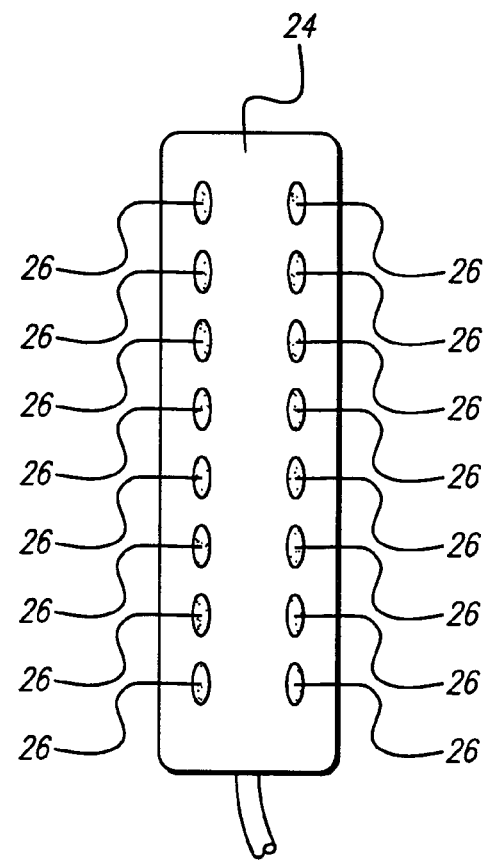
FIG. 3B shows a paddle-type electrode array used to provide two dimensional stimulation.

As shown in FIG. 3A, an SCS system 10 may use a single in-line electrode array (one dimensional) or may use two or more in-line arrays 20 to create a two dimensional array of electrodes 22. As shown in FIG. 3B, an SCS system 10 may also use a single paddle array 24 with two or more columns of electrodes 26 to create a two dimensional array. Multiple in-line arrays 20 or multiple paddle arrays 24 may be connected to an IPG 12 like the IPG 12 shown in FIG. 1.

A stimulation space is the region which may be stimulated by all possible combinations of electrodes of the electrode arrays 20 and 24. Although the electrode arrays 20 and 24 are three dimensional and are arranged in a three dimensional manner, arrays 20 and 24 are generally implanted in a side-by-side manner that is relatively two dimensional. The stimulation space is thus described in the following description of the present invention as being two dimensional, even though the stimulation space is technically three dimensional. The two dimensional description is not intended to limit the present invention to cases where the electrode arrays reside on a flat surface; such description is merely used for convenience of describing the relative orientations of the present invention and its surrounding environment.

Figure 4A:
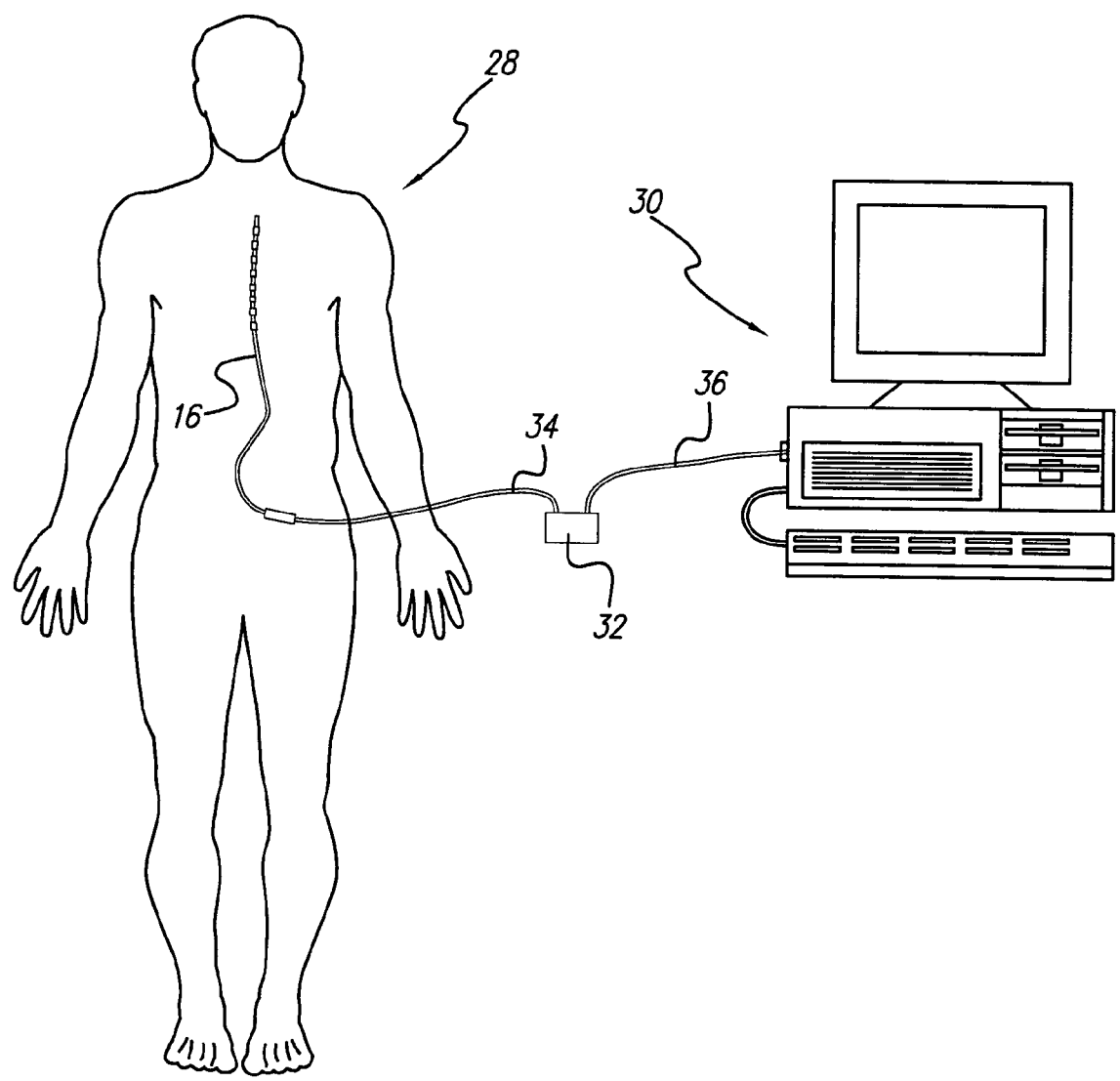
FIG. 4A shows a first equipment suite suitable for SCS system fitting during a trial phase wherein an External Trial Stimulator (ETS) is connected to the electrode array using a percutaneous cable.

As shown in FIG. 4A, the SCS system 10 (see FIG. 1) is partially implanted in a patient 28 and connected to a programming computer 30 during fitting. A fitting suite used during initial implantation includes an External Trial Stimulator (ETS) 32 electrically connected by an external or percutaneous cable 34 to the electrode lead 16. The electrode lead 16 is implanted into the epidural space of the patient's 28 spine. A second cable 36 connects the ETS 32 to the programming computer 30. ETS 32 also may communicate with the programming computer 30 using a radio frequency (RF) link, an infrared (IR) link, or some other wired or wireless communications method.

Figure 4B:
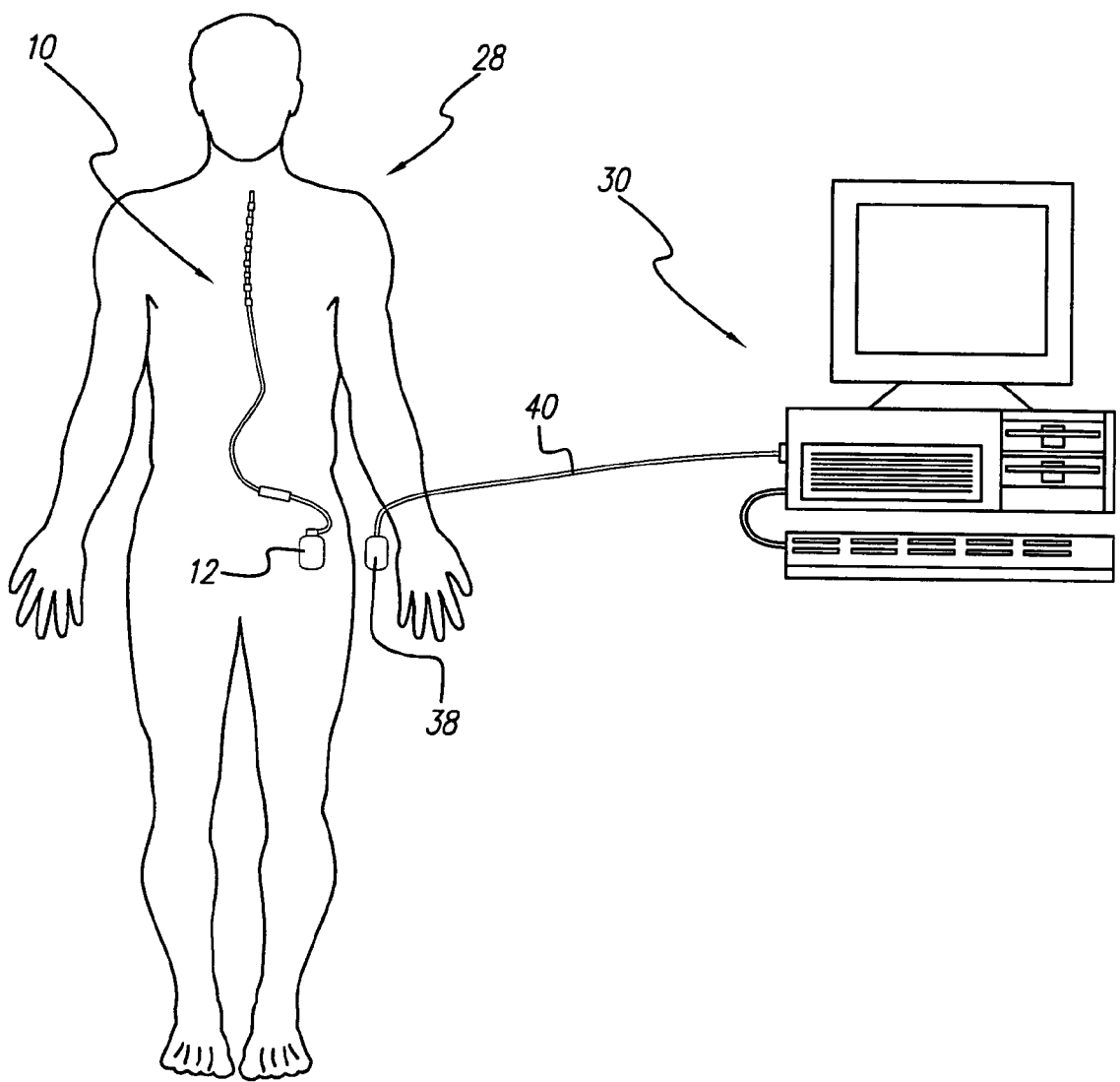
FIG. 4B shows a second equipment suite suitable for SCS system fitting after implantation of a permanent stimulation system.

As shown in FIG. 4B, the SCS system 10 is later entirely implanted in a patient 28 for normal use. A second fitting suite shown in FIG. 4B is used following implantation of the IPG 12. The second suite includes a hand held programmer 38, or other communications device, which wirelessly communicates through the skin with the IPG 12. The programmer 38 also may communicate with the programming computer 30 using a third cable 40, an RF link, an IR link, or some other wired or wireless communications method.

The method of the present invention may be exercised in the context of the first fitting suite, the second fitting suite, or any other equipment adaptable to the fitting procedure. Use of the present invention with any fitting procedure using any equipment is intended to come within the scope of the present invention.

A stimulation configuration includes at least the following parameters: electrode combination, pulse width, pulse amplitude, pulse frequency, and electrode polarity. The overall effect and power consumption of the stimulation is determined by the selection of these parameters. As mentioned earlier, at least one electrode may be configured, or located, on a single array or multiple arrays and placed in virtually any orientation within the epidural space of the spine. Generally, the pulse width and the pulse frequency are selected and fixed prior to a fitting procedure. During the fitting procedure, a clinician determines the pulse amplitude, or current level, and the electrodes used for stimulation (during current steering). Current steering refers to the selection of (an) electrode(s) to act as (a) means for delivering current to the body. If a single in-line array is used during a fitting procedure with either fitting suite mentioned above in FIGS. 4A and 4B, the stimulation may be steered longitudinally (vertically) by delivering stimulation through a subset of electrodes of the electrode array 18, to find effective locations for stimulation. When a two dimensional electrode array is used to provide stimulation (i.e., the two or more in-line arrays 20 or the paddle array 24), the stimulation may be steered both longitudinally (vertically) and laterally (horizontally) by delivering stimulation through a two-dimensional subset of the electrodes.

The extra degree of freedom provided by a two dimensional array facilitates improved stimulation. But, the search for the best location for stimulation may complicate and/or lengthen the SCS system 10 fitting procedure. Many stimulation locations and configurations may provide effective stimulation, but the power consumption of each of the effective locations and configurations may vary substantially. One tool used to guide a clinician during the fitting procedure is a navigation display as described in U.S. Pat. No. 6,393,325, issued May 21, 2002, entitled "Directional Programming for Implantable Electrode Arrays."

Figure 5A:
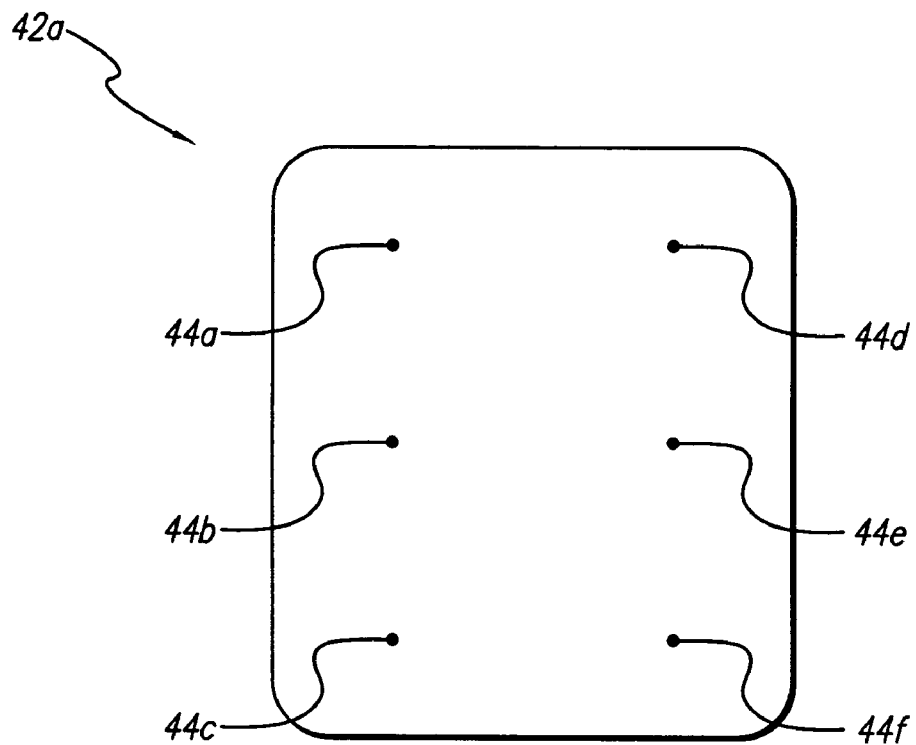
FIG. 5A shows a preliminary navigation screen adapted to display power consumption data.
Figure 5B:
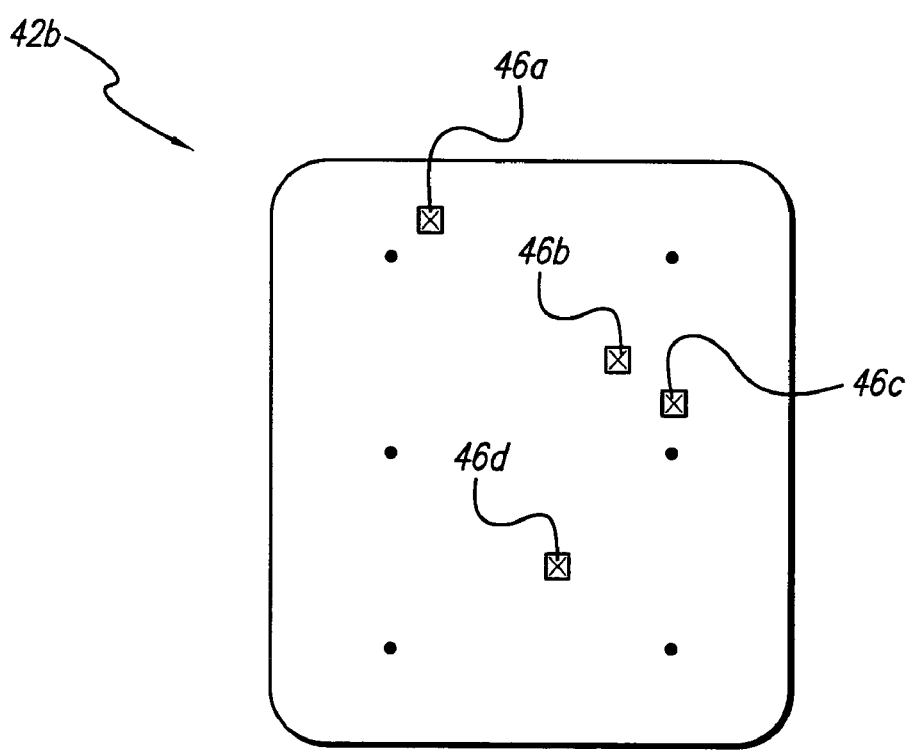
FIG. 5B shows a navigation screen after additional configurations have been tested.

In an improved navigation display according to the present invention, exemplified in FIGS. 5A and 5B, the power consumption adequate for effective stimulation may be represented on the navigation display by various methods. For example, an improved navigation display may include individual points indicating power consumption levels which may be marked, or labeled, numerically; textually; by color; by intensity; by area, i.e., by visually modifying a proportionate number of pixels; graphically; or otherwise. Alternately, power consumption levels may be represented by audible signals, or labels, that vary in pitch, volume, tone, number, or length. These labels, or markers, serve to communicate the various levels of power consumption related to various stimulation configurations explored by a clinician. The number of labels may vary, and preferably provide a clear and proportionate representation actual measurements of power consumption required for effective stimulation. A location where stimulation was attempted, but effective stimulation was not achieved, may or may not be labeled.

As shown in FIG. 5A, a preliminary navigation display 42a is created and may typically include individual points 44a, 44b, 44c, 44d, 44e, and 44f which represent stimulation configurations. One method of generating the preliminary navigation display 42a is to provide a joystick type control to the patient, wherein the joystick controls at least the stimulation level (i.e., the pulse current level or amplitude). The patient may use the joystick to adjust the stimulation level to determine an adequate stimulation level for effective stimulation. The patient indicates effective stimulation has been achieved, and the adequate stimulation level is recorded and used to generate the audio or visual label, or indicator, of power consumption. The label is then associated with point on the navigation display 42a so as to be presently or readily available when the clinician is viewing a particular point on the navigation display.

During a typical preliminary stage of the fitting procedure, a small number of preliminary configurations, or points, may be tested, for example, six. An example of data that results in the points 44a-44f are presented in Table 1. The coordinates of the points in Table 1 may correspond to locations of a specific polarity of the electrodes, i.e., cathodes (negatively charged electrodes) or anodes (positively charged electrodes). The electrodes may be on a two dimensional array of electrodes 22 (FIG. 3A) or a single paddle array 24 with two or more columns (FIG. 3B).

TABLE 1

Preliminary Navigation Display Points

| Point Number | X Coordinate | Y Coordinate | Power Consumption |
| --- | --- | --- | --- |
| 1 (44a) | −0.50 | +1.50 | 3.0 |
| 2 (44b) | −0.50 | 0.00 | 3.2 |
| 3 (44c) | −0.50 | −1.50 | 2.4 |
| 4 (44d) | +0.50 | +1.50 | 3.0 |
| 5 (44e) | +0.50 | 0.00 | 3.8 |
| 6 (44f) | +0.50 | −1.50 | 3.1 |

Several methods may be used to convert current levels to power consumption values for use with the navigation display 42a. For example, prior to obtaining measurements used to generate the navigation display 42a, an impedance (R) may be measured for the points 44a-44f. The measured impedance may be used to calculate the power (P) consumptions of each of the points 44a-44f using the following power formula:

$$P=(I^2*PW^2*PR^2*R)+B$$

where:

I is a primary pulse train amplitude, i.e., pulse current level;

PW is a pulse width of a primary stimulation pulse;

PR is a pulse repetition rate;

R is the measured impedance; and

B is a background power drain required to maintain stimulation.

Interpolation and/or extrapolation may be used to estimate the adequate stimulation levels at secondary points on the navigation display that were not tested. The impedance for all stimulation configurations used in the fitting procedure may be measured prior to the fitting procedure or estimated based on the total surface area of the electrodes in the combination and the relative current density on each electrode. The power consumptions at the secondary points may be computed using the power formula with the estimated adequate stimulation level, the measured or estimated impedance, and the background current needed to maintain the stimulation.

The estimate of power consumption may be improved by either incorporating the background power consumption of a charge pump (in the case of controlled voltage stimulators) or by modeling the circuitry necessary to maintain the stimulator compliance voltage due to both resistive and reactive electrode impedances (in the case of controlled current stimulators).

Once the preliminary navigation display 42a is complete, the points 44a-44f may be used as an aid in the selection of a configuration for use by the SCS system 10. The point with the lowest power consumption may be selected for patient use or the power consumption may be considered along with other parameters or effects to select a stimulation configuration for patient use. Alternately, the measured effective stimulation configurations, e.g., represented by the points 44a-44f, stored in the preliminary navigation display may be used as a starting point in a procedure to determine a low power consumption configuration and/or stimulation parameter setting. During the search for a low power consumption configuration, the navigation display 42a may be refined. As the patient and/or clinician navigates through the stimulation space, the patient and/or clinician may also control the stimulation level to maintain effective stimulation (sensory paresthesia in the case of SCS). As a result, the stimulation level required for effective stimulation may be determined at each location visited in the stimulation space. In this manner, the navigation display 42a may be refined by calculation of the power consumption of each point visited by the patient and adding or replacing that point to the navigation display 42a.

Additionally, as indicated in FIG. 5B, as the patient and/or clinician navigates, he/she/they may indicate several configuration and/or parameter settings that provide effective stimulation. These configurations may be represented by points 46a-46d on the navigation display 42b. When the patient and/or clinician has finished navigating the stimulation space, he/she may revisit these marked "best" points 46a-46d in the stimulation space. Often, a patient may have no subjective preference between several marks. The clinician may then use the power qualifiers in the navigation display 42a or 42b to select the stimulation configuration with the lowest power consumption.

Another method of guiding a search for a low power consumption configuration includes using a navigation display such as 42a or 42b, or another communication device, with audio or visual labels that indicate power consumption level as a guide to find other potentially effective stimulation configurations. The navigation display or communication device indicates, or suggests, other potential directions for navigation. The clinician may then select a direction for the patient to navigate in, based on the audio or visual representation. For example, at the start of navigation, the patient may identify a preferred point corresponding with effective stimulation, and the clinician may direct the patient to search for a better point around the preferred point based on the slope of the power consumption around the preferred point.

Figure 6:
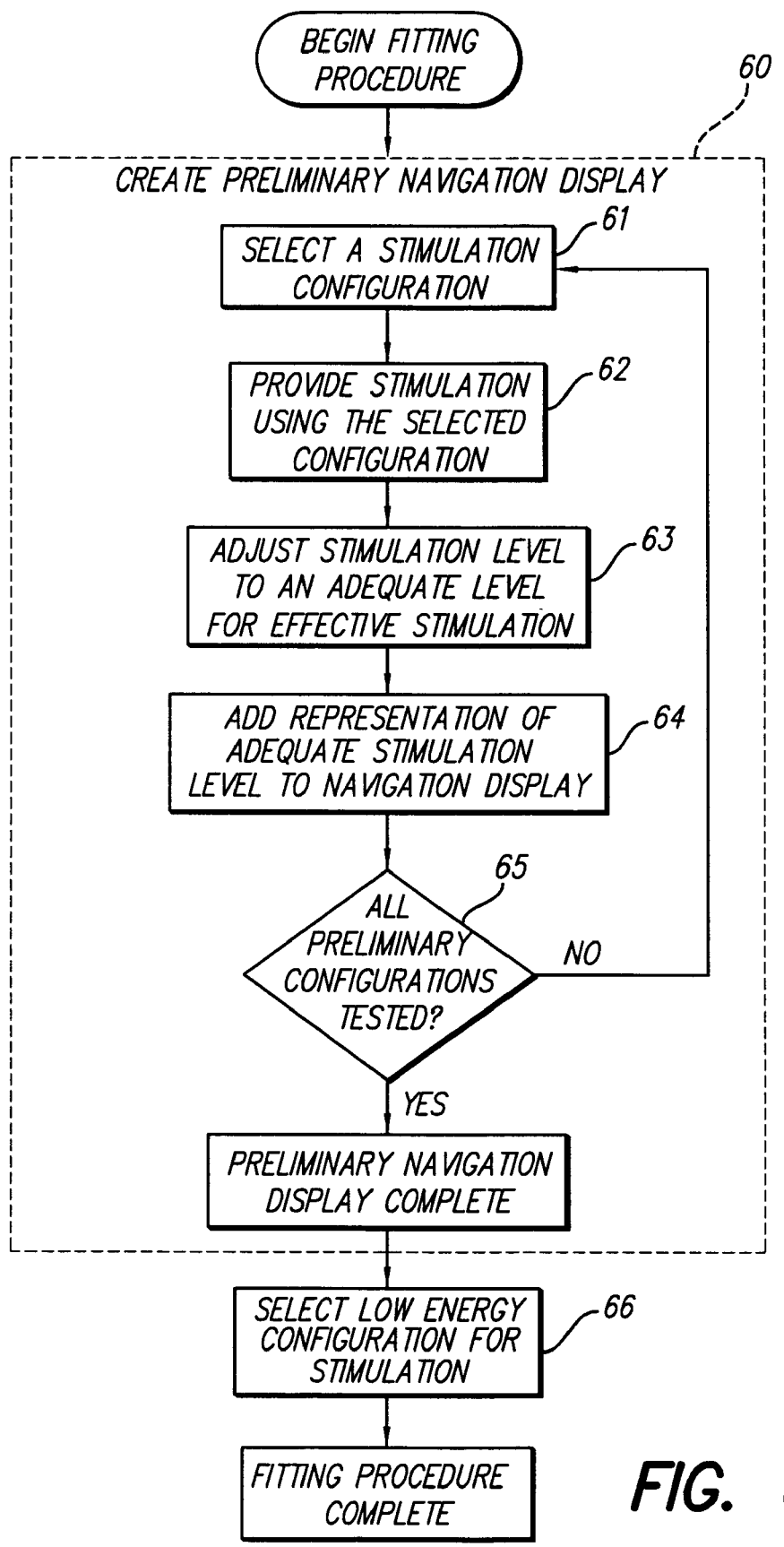
FIG. 6 depicts a method of using power consumption levels displayed on a navigation screen to guide a clinician's selection of a low power consumption stimulation configuration.

As depicted in FIG. 6, an example of a first method, according to the present invention, for selecting a stimulation configuration based on a set of preliminary measurements may be described as follows:

(a) beginning a fitting procedure;

(b) testing all preliminary configurations (block 65) by repeating the following steps for each of a set of preliminary configurations in order to create at least one preliminary navigation display (block 60):

(1) selecting a stimulation configuration (block 61) with set parameters that may include: pulse location, pulse width, pulse frequency, and electrode polarity;

(2) providing stimulation using the selected configuration (block 62);

(3) adjusting the stimulation level, i.e., the pulse current level, or amplitude, to a level adequate for effective stimulation (block 63); and (4) adding a representation of the adequate stimulation level to the navigation display (block 64); and (c) selecting a configuration for use by the patient (block 66) based, at least in part, on power consumption level.

The step of (4) adding a representation of the adequate stimulation level to the navigation display (block 64) may include (i) calculating a power consumption level as a function of the adequate stimulation level and (ii) updating the navigation display with the power consumption.

Figure 7:
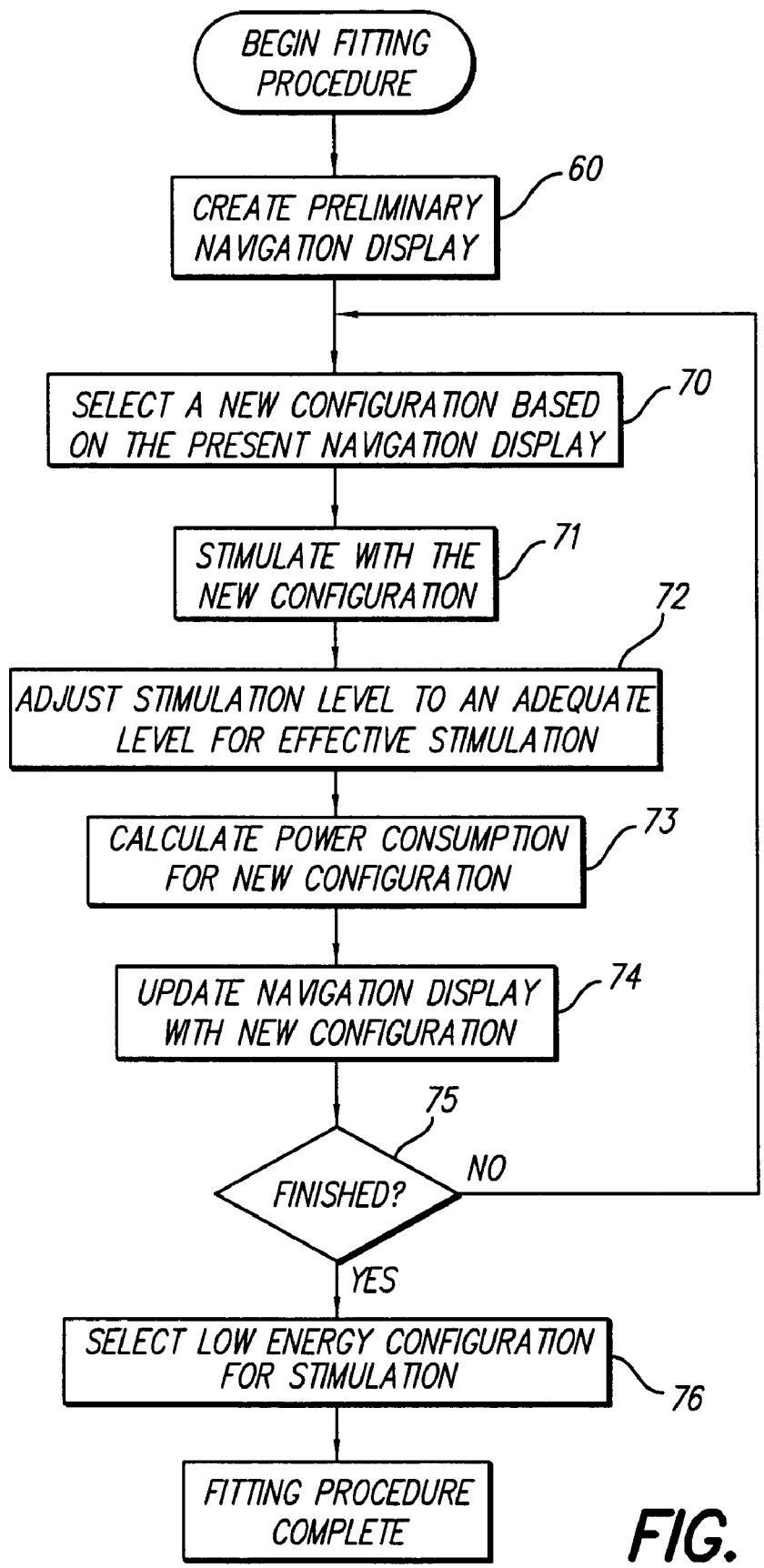
FIG. 7 depicts a method of using power consumption levels displayed on a navigation screen to guide a clinician's search for a low power consumption stimulation configuration.

As depicted in FIG. 7, an example of a second method, according to the present invention, for selecting a stimulation configuration using a search based on a set of preliminary measurements may be described as follows:

(a) beginning a fitting procedure;

(b) creating a preliminary navigation display (block 60, described in FIG. 6);

(c) repeating the following steps for at least one new configuration:

(1) selecting a new configuration based on suggested feedback from the present navigation display (block 70), which feedback directs the clinician and/or patient to a configuration with potentially more effective parameters and/or results;

(2) stimulating with the new configuration (block 71);

(3) adjusting the stimulation, i.e., the pulse current level, to an adequate level for effective stimulation (block 72);

(4) calculating the power consumption for the new configuration (block 73);

(5) updating the navigation display with the new configuration (block 74);

(6) repeating the steps of block 70 through 74, i.e., steps (1) through (5), if an adequate stimulation configuration has not been determined and the clinician and/or patient is not finished (block 75); and (d) selecting a configuration from the updated navigation display (block 76).

The methods of the present invention may be applied to the selection, or modification, of any of the members of the stimulation parameter set. For example, the pulse width, and/or the pulse frequency may be varied and the adequate power consumption resulting in effective stimulation may be communicated to the clinician and/or patient and modified by the clinician and/or patient, thereby modifying the characteristics of the stimulation parameter set.

While the invention herein disclosed has been described by means of specific embodiments and applications thereof, numerous modifications and variations could be made thereto by those skilled in the art without departing from the scope of the invention as set forth in the claims.

What is claimed is:

1. A method for determining a low power consumption stimulation parameter set for stimulating a patient, comprising:

(a) obtaining a stimulation parameter set;

(b) providing stimulation to a selected region of a spinal cord in accordance with the stimulation parameter set;

(c) obtaining a level of power consumption of the stimulation parameter set;

(d) associating the level of power consumption with the stimulation parameter set;

(e) repeating steps (a) through (d) for each of a plurality of different stimulation parameter sets, wherein at least some of the different stimulation parameter sets have different electrode configurations; and (f) determining the low power consumption stimulation parameter set based, at least in part, on the levels of power consumption respectively associated with the different stimulation parameter sets.

2. The method of claim 1 wherein obtaining the stimulation parameter set comprises:

selecting one of a multiple of stimulation parameter sets;

adjusting the stimulation level of the one stimulation parameter set to find an adequate stimulation level for achieving sensory paresthesia.

3. The method of claim 1 wherein obtaining the level of power consumption comprises computing a value of the power consumption.

4. The method of claim 1 wherein the low power consumption stimulation parameter set is selected from the different stimulation parameter sets.

5. The method of claim 4 further comprising displaying representations of the different stimulation parameter sets and associated levels of power consumption to a user, wherein the user selects the low power consumption stimulation parameter set from the displayed stimulation parameter set representations.

6. The method of claim 1 further comprising programming the low power consumption stimulation parameter set into a spinal cord stimulation (SCS) implantable pulse generator (IPG).

7. A system for determining a low power consumption stimulation parameter set for stimulating a patient, comprising:

an electrical pulse generator configured for providing stimulation to a selected region of the spinal cord in accordance with a plurality of different stimulation parameter sets, wherein at least some of the different stimulation parameter sets have different electrode configurations; and a programming device configured for associating levels of power consumption respectively with the different stimulation parameter sets, and determining the low power consumption stimulation parameter set based, at least in part, on the levels of power consumption respectively associated with the different stimulation parameter sets.

8. The system of claim 7 further comprising a spinal cord stimulation (SCS) electrode lead coupled to the electrical pulse generator.

9. The system of claim 7 wherein the electrical pulse generator is an external trial stimulator (ETS).

10. The system of claim 7 wherein the programming device is further configured for allowing a user to adjust the stimulation levels of stimulation parameter sets to find adequate stimulation levels achieving sensory paresthesia for the different stimulation parameter sets.

11. The system of claim 7 wherein the programming device is further configured for computing the values of power consumption, respectively associating the computed values of power consumption with the different stimulation parameter sets, and determining the low power consumption stimulation parameter set based, at least in part, on the values of power consumption respectively associated with the different stimulation parameter sets.

12. The system of claim 7 further comprising a user interface configured for allowing a user to select the low power consumption stimulation parameter set from the different stimulation parameter sets.

13. The system of claim 12 wherein the user interface is further configured for displaying representations of the different stimulation parameter sets and associated levels of power consumption to a user.

14. The system of claim 7 further comprising a lead carrying a plurality of electrodes configured for being placed along the spinal cord, wherein the electrical pulse generator mated with the lead and is configured for providing stimulation to the selected region of the spinal cord via the electrodes in accordance with the different stimulation parameter sets.

15. The system of claim 7 wherein the programming device is configured for programming the low power consumption stimulation parameter set into a spinal cord stimulation (SCS) implantable pulse generator (IPG).

16. A method for determining a low power consumption stimulation parameter set for stimulating a patient, comprising:
   (a) obtaining a stimulation parameter set;
   (b) providing stimulation to the patient in accordance with the stimulation parameter set;
   (c) obtaining a level of power consumption of the stimulation parameter set;
   (d) associating the level of power consumption with the stimulation parameter set;
   (e) repeating steps (a) through (d) for each of a plurality of different stimulation parameter sets, wherein at least some of the different stimulation parameter sets have different electrode configurations; and
   (f) determining the low power consumption stimulation parameter set based, at least in part, on the levels of power consumption respectively associated with the different stimulation parameter sets.

17. The method of claim 16 wherein each of the different electrode configurations comprises a location of a specific polarity of the electrodes.

18. The method of claim 16 wherein obtaining the stimulation parameter set comprises:
   selecting one of a multiple of stimulation parameter sets;
   adjusting the stimulation level of the one stimulation parameter set to find an adequate stimulation level for achieving effective stimulation.

19. The method of claim 16 wherein obtaining the level of power consumption comprises computing a value of the power consumption.

20. The method of claim 19 wherein the low power consumption stimulation parameter set is selected from the different stimulation parameter sets.

21. The method of claim 16 further comprising displaying representations of the different stimulation parameter sets and associated levels of power consumption to a user, wherein the user selects the low power consumption stimulation parameter set from the displayed stimulation parameter set representations.

22. The method of claim 16 further comprising programming the low power consumption stimulation parameter set into an implantable pulse generator (IPG).

23. A system for determining a low power consumption stimulation parameter set for stimulating a patient, comprising:
   an electrical pulse generator configured for providing stimulation to the patient in accordance with a plurality of different stimulation parameter sets, wherein at least some of the different stimulation parameter sets have different electrode configurations; and
   a programming device configured for associating levels of power consumption respectively with the different stimulation parameter sets, and determining the low power consumption stimulation parameter set based, at least in part, on the levels of power consumption respectively associated with the different stimulation parameter sets.

24. The system of claim 23 further comprising an electrode lead coupled to the electrical pulse generator.

25. The system of claim 23 wherein the electrical pulse generator is an external trial stimulator (ETS).

26. The system of claim 23 wherein the electrical pulse generator comprises a joystick configured for allowing a user to adjust the stimulation levels of stimulation parameter sets to find adequate stimulation levels achieving sensory paresthesia for the different stimulation parameter sets.

27. The system of claim 23 wherein the programming device is further configured for computing the values of power consumption, respectively associating the computed values of power consumption with the different stimulation parameter sets, and determining the low power consumption stimulation parameter set based, at least in part, on the values of power consumption respectively associated with the different stimulation parameter sets.

28. The system of claim 23 further comprising a user interface configured for allowing a user to select the low power consumption stimulation parameter set from the different stimulation parameter sets.

29. The system of claim 28 wherein the user interface is further configured for displaying representations of the different stimulation parameter sets and associated levels of power consumption to a user.

30. The system of claim 23 wherein at least some of the different stimulation parameter sets have different electrode configurations.

31. The system of claim 23 wherein the programming device is configured for programming the low power consumption stimulation parameter set into an implantable pulse generator (IPG).

* * * * *